United States Patent [19]

Clardy et al.

[11] 4,215,563
[45] Aug. 5, 1980

[54] CHROMATOGRAPHIC ANALYSIS NORMALIZER

[75] Inventors: Edwin K. Clardy; Buell O. Ayers, both of Bartlesville, Okla.

[73] Assignee: Phillips Petroleum Company, Bartlesville, Okla.

[21] Appl. No.: 705,486

[22] Filed: Jul. 15, 1976

[51] Int. Cl.² .............................................. G01N 31/08
[52] U.S. Cl. ........................................................ 73/23.1
[58] Field of Search .......... 73/23.1; 23/232 C, 254 R; 422/98

[56] References Cited

U.S. PATENT DOCUMENTS

| Re. 24,876 | 9/1960 | Coggeshall | 73/23.1 |
|---|---|---|---|
| 3,121,160 | 2/1964 | Burk | 73/23.1 |
| 3,126,731 | 3/1964 | Armstrong | 73/23.1 |
| 3,177,138 | 4/1965 | Larrison | 73/23.1 |
| 3,208,230 | 9/1965 | Fourroux | 73/23.1 |
| 3,449,556 | 6/1969 | Clardy | 73/23.1 |
| 3,686,923 | 8/1972 | Favre | 73/23.1 |
| 3,698,237 | 10/1972 | Rhodes | 73/23.1 |

Primary Examiner—Stephen A. Kreitman

[57] ABSTRACT

In a chromatographic analysis system a bypass conduit operating in parallel with a chromatographic separation column diverts a portion of the sample fluid directly to the chromatographic detector prior to elution through the chromatographic separation column of the remaining portion of the sample material. Comparison of the detector response to the bypassed portion of the sample with the detector response to selected constituents or groups of constituents exiting the chromatographic separation column is used to normalize the analysis response to one or more constituents or groups of constituents eluted through the chromatographic separation column.

12 Claims, 4 Drawing Figures

CHROMATOGRAPHIC ANALYSIS NORMALIZER

This invention relates to a method and apparatus for fluid chromatographic separation and analysis. In another aspect the invention relates to a method and apparatus for normalizing the response of a chromatographic analysis system. In still another aspect the invention relates to a method and apparatus for automatically normalizing a chromatographic analyzer output. In yet another aspect the invention relates to a method and apparatus for normalizing a plurality of related sequential telemetry signals.

Chromatographic analysis techniques are useful in providing a quantitative determination of the composition of a fluid sample. For successive samples of predetermined size, the relative proportions of individual constituents or groups of constituents separated by a packed chromatographic column are often determined directly from the response of a chromatographic detector to the passage of the sample constituents or groups of constituents therethrough, after initial calibration of the analysis system has been completed. In applications where the size of the sample injected into the chromatographic analysis apparatus is subject to significant variation, calibration of the system to permit direct conversion of the chromatographic detector response to any preselected constituent or group of constituents is not possible. In analysis applications where such variations in sample size are expected, the usual method of determining the relative proportions of individual constituents of groups of constituents within the sampled fluid is to sum the detector response to all portions of the sample fluid passing therethrough by, for example, continuously integrating the detector response until such time as the entire sample has eluted through the chromatographic column, then comparing individual chromatographic peaks representing preselected constituents or groups of constituents to the entire sample response. Such a procedure, however, has the disadvantage of requiring all constituents to have eluted through the chromatographic column and passed through the detector before a determination can be made regarding the amount of any particular constituent or group of constituents within the sample. In addition, when the sample contains one or more constituents exhibiting extremely long elution times, the time following injection of the sample at which the meaning of the initial chromatographic peaks can be meaningfully interpreted is further delayed and/or additional equipment is required to backflush the chromatographic column in order to insure that all portions of the sample are presented to the chromatographic detector. Even when the greatest possible care is taken to insure that all portions of the sample are presented to the detector, some constituents present in relatively minute amounts may, due to the sensitivity or accuracy of the particular detector and detector response accumulation techniques and equipment, escape accurate inclusion in the overall determination of total sample content. The difficulties described hereinabove are most easily recognized in systems wherein individual samples of the same nominal size are introduced into a chromatographic analysis system by sampling techniques of obviously limited precision such as injection of samples into an analysis apparatus by means of a hypodermic needle in a laboratory analysis system. However, the same problems exist in sampling systems generally considered to be precise enough to permit use of an initial system calibration followed by direct determination of sample content directly from the individual constituent peaks detected. For example, some manufacturers' sample valves will, under process operating conditions, permit a variation in sample size on the order of about 1 percent. Such variations can be caused by the construction of the sample valve itself, variations in pressure of the sampled fluid, or other similar circumstances. While such relatively small variations in sample size can be tolerated in some applications without harmful effect, the increasing sophistication of automatic control systems and the need for automatic analysis equipment and methods for use in conjunction with such systems, as well as for laboratory use, make it desirable to provide a chromatographic analysis method and apparatus of improved accuracy.

It is therefore an object of the invention is to provide a method and apparatus for fluid chromatographic separation and analysis. Another object of the invention is to provide a method and apparatus for normalizing the response of a chromatographic analysis system. Still another object of the invention is to provide a method and apparatus for automatically normalizing a chromatographic analyzer output. Yet another object of the invention is to provide a method and apparatus for normalizing a plurality of related sequential telemetry signals.

In accordance with the invention, a method and apparatus are provided whereby a bypass column is connected in parallel with the chromatographic separation column of a chromatographic analysis apparatus to provide bypass flow of a predetermined portion of fluid around the chromatographic separation column directly to the chromatographic detector. The remaining portion of the sample fluid flows into the chromatographic separation column and is eluted therethrough to the chromatographic detector. In addition to providing a bypass column of a size suitable for dividing the flow of fluid through the parallel combination of the separation and bypass columns, and thus any sample fluid introduced thereto, into first and second portions having a predetermined relative size one to the other, the bypass column is sized to provide passage of sample fluid therethrough prior to elution of any portion of the sample material through the packed chromatographic separation column. The unseparated portion of the sample fluid flowing through the bypass column therefore arrives at the chromatographic detector means and passes therethrough prior to arrival of the first peak from the chromatographic separation column at the detector.

Since the portion of sample fluid entering the detector from the bypass column bears a known size relationship to the portion of the sample fluid which enters the chromatographic separation column, the response of the chromatographic detector to the sample fluid exiting the bypass column can be used as a measure of the size of the sample to be separated. The detector response to the portion of sample material entering from the bypass column will therefore be a signal from which information indicative of the total amount of sample material passing through the bypass column can be obtained, and application of an appropriate constant factor to such a detector response will result in the generation of a signal from which information relating to the amount of sample fluid passing through the chromatographic separation column or the total amount of fluid sample introduced into the analysis apparatus can be obtained. As each of the peaks representing a constituent or group of constituents exiting the chromatographic separation column is provided by the chromatographic detector, the information provided by such responses can be immediately compared with the information provided by the initial detector response to the unseparated sample material from the bypass column, and an immediate determination of the relative amount of the constituent or constituents represented by each chromatographic peak, corrected for any variations in sample size, can be made. As each separated constituent or group of constituents exits the chromatographic separation column, therefore, the signal can be adjusted for variations in sample size or normalized and can thereafter be immediately used for control purposes without having to wait for the remaining sample constituents to be eluted through the chromatographic column to determine the total sample size. When only one or a few constituents or constituent groups are of significance, a chromatographic separation column for rapidly separating only those peaks of interest can be advantageously used to save analysis time while providing an accurately normalized determination of the presence of the separated constituents. In addition, constituents present in relatively minute quantities which might otherwise be provided to the chromatographic detector in amounts small enough to escape accurate detection due to the sensitivity of the particular detection system will be included together with all other constituents in the portion of the sample fluid entering the detector from the bypass column for the purpose of generating a signal from which the total sample size can be determined. Also, use of additional equipment otherwise needed to backflush slow eluting constituents through the detector from the separation column to obtain a measure of total sample size, even though such slow eluting constituents may be of no other interest, can be avoided.

Other objects and advantages of the invention will be apparent from the description of the invention and appended claims thereto as well as from the detailed description of the drawings in which:

Figure 1:
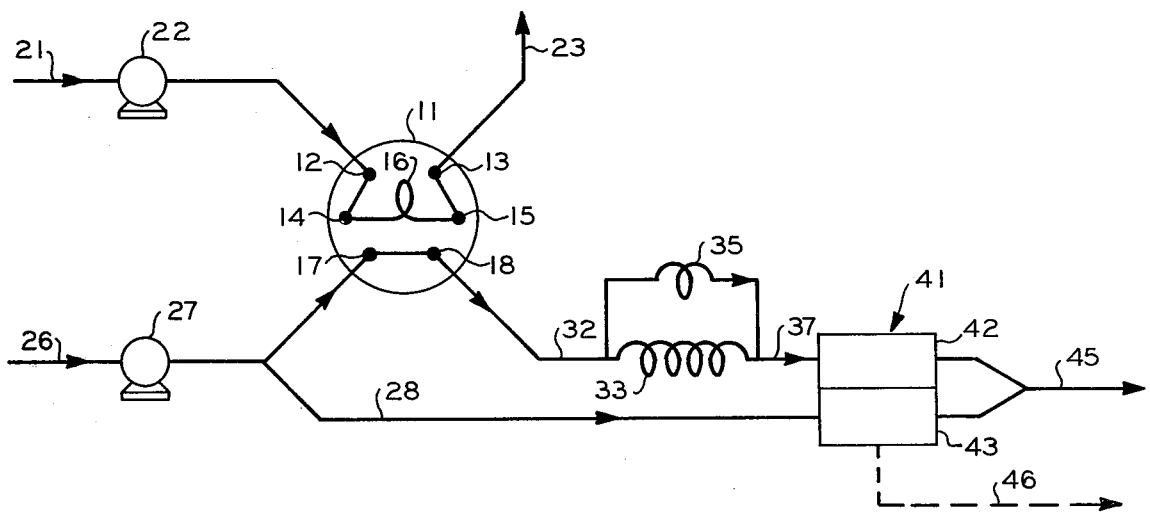
FIG. 1 is a schematic representation of a chromatographic sampling, separation, and detection apparatus constructed in accordance with the invention.

Referring to FIG. 1, there is illustrated a chromatographic sample valve means 11 having associated therewith a sample inlet port 12, a sample outlet port 13, a pair of sample loop ports 14 and 15 having a sample loop 16 of preselected volume connected therebetween, a carrier inlet port 17, and a carried outlet port 18. A sample source conduit 21 is operably connected in fluid communication with the sample inlet port 12 through a sample pump means 22 for providing a supply of sample fluid under suitable pressure to the sample inlet port 12 of the sample valve means 11. A sample disposal conduit 23 is operably connected in fluid communication with the sample outlet port 13 to provide for disposal of sample fluid exiting the sample valve means 11.

A carrier supply conduit means 26 in fluid communication with a suitable source of chromatographic carrier fluid (not shown), and a pump means 27 provide a source of chromatographic carrier fluid under pressure to the carrier inlet port 17 of the sample valve means 11 and to a reference fluid conduit 28.

With the sample valve means 11 in its first position as illustrated by FIG. 1, the sample fluid from the sample fluid conduit 21 flows into the sample inlet port 12, to the sample loop port 14, through the sample loop 16 to the sample loop port 15, to the sample outlet port 13, and through the sample outlet conduit 23 to a suitable sample fluid recycle or disposal means (not shown). Meanwhile, the carrier fluid enters the carrier inlet port 17 and is conveyed to the carrier outlet port 18 for delivery to an analysis conduit 32. When the sample valve means 11 is switched to its second position, its internal communication between ports 12 and 14, 13 and 15, and 17 and 18 is terminated and communication between ports 12 and 13, 14 and 17, and 18 and 15 is established, thereby injecting the fluid sample contained within the sample loop 16 into the carrier stream entering the sample valve means 11 through the carrier inlet port 17 and exiting through the carrier outlet port 18 and analysis conduit 32.

The sample fluid thus introduced into the analysis conduit 32 is provided to the parallel combination of a chromatographic separation conduit 33 and a bypass conduit 35. The chromatographic separation conduit 33 and be any suitable chromatographic separation column capable of providing the desired separation of constituents or groups of constituents within the sample fluid. The bypass column 35 is preferably of such length and provides such restriction to flow that the flow rate of carrier fluid and sample fluid therethrough bears a predetermined relationship to the flow rate of carrier fluid and sample fluid through the chromatographic separation column 33 while also providing for passage of carrier and sample fluids therethrough in a period of time which is short enough to provide for passage of sample material from the bypass conduit 35 to the downstream confluence of the bypass conduit 35 and separation conduit 33 prior to arrival at such downstream confluence of any portion of the sample material eluted through the chromatographic separation column 33.

While any suitable relative flow rates between the chromatographic separation column 33 and bypass column 35 can be used, the use of a bypass column flow to separation column flow ratio with a range of from about 1:10 to about 1:1 is presently preferred, with ratios within the range of from about 1:5 to about 1:1 being particularly preferred and a ratio of about 1:1 being most preferred. Any suitable arrangement of column sizing can be utilized to achieve such ratios. For example, the chromatographic separation column 33 is ordinarily selected to provide the desired separation and degree of separation with the bypass column 35 being adjusted by means of incorporation of capillary tubing, other similar small sized tubing, or packing material capable of presenting a resistance to flow but incapable of seriously delaying any of the sample constituents. These and other similar techniques can be used to adjust the rate of flow through the bypass column 35 so that the desired division of sample material between the separation column 33 and bypass column 35 is achieved.

In addition, the total effective length of the bypass column 35 is preferably such that the peak of unresolved sample material passing through the bypass column 35 to the detector means 41 will arrive at the detector means 41 and pass therethrough well in advance of the arrival at the detector means 41 of the first portion of sample material eluted through the chromatographic separation column 33. Such a timing arrangement will insure separation of the peak representing the bypassed sample from the peaks representing the eluted sample in the chromatographic detector output signal 46. Initial flow calibration and flow calibration checks can be accomplished by operating the system using a standard sample fluid consisting of a single rapid eluting constituent.

At the downstream confluence of the parallel chromatographic separation column 33 and bypass column 35 a downstream conduit 37 accepts the combined flows of the separation and bypass conduits and provides the combined flow to the sample cell 42 of a detector means 41 having a sample cell 42 and a reference cell 43. The detector means 41 can be any suitable chromatographic detector such as a differential refractometer, a differential thermal conductivity cell, or other suitable detector means. Although a detector means 41 employing both a sample cell 42 and a reference cell 43 wherein the difference between the characteristics of the carrier fluid entering the reference cell 43 and the sample-containing carrier fluid entering the sample cell 42 produces a detector output signal 46 has been illustrated, the use of a suitable detector means 41 which is not of a differential nature and employs only a single sample cell, such as a flame ionization detector, is within the scope of the invention. The effluent streams from the reference cell 43 and sample cell 42 can be combined and provided through a disposal conduit 45 for suitable disposition as known in the art.

Figure 2:
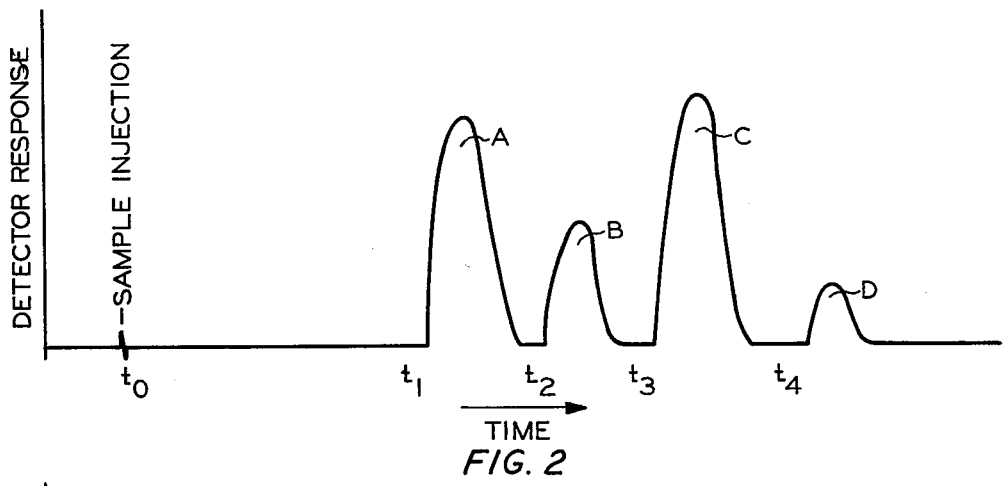
FIG. 2 is a schematic representation of a standard chromatographic detector response to an eluted sample fluid.

FIG. 2 is a schematic illustration of the form of output signal 46 from the chromatographic detector means 41 which would be generated in response to a typical chromatographic separation not employing the bypass column 35 of the present invention. As can be seen from the FIGURE, at some time $t_1$ following the injection of a sample into the analysis system at time $t_0$ the first of the sample constituents or group of constituents eluted through the chromatographic separation column arrives at the detector to produce a first chromatographic output peak A. When the chromatographic separation column is selected so that substantially complete separation of successive constituents or groups of constituents eluted therefrom is achieved, there will be times $t_2$, $t_3$, $t_4$ preceding each of the successive chromatographic peaks B, C, D, during which the output signal of the chromatographic detector is substantially zero.

Figure 3:
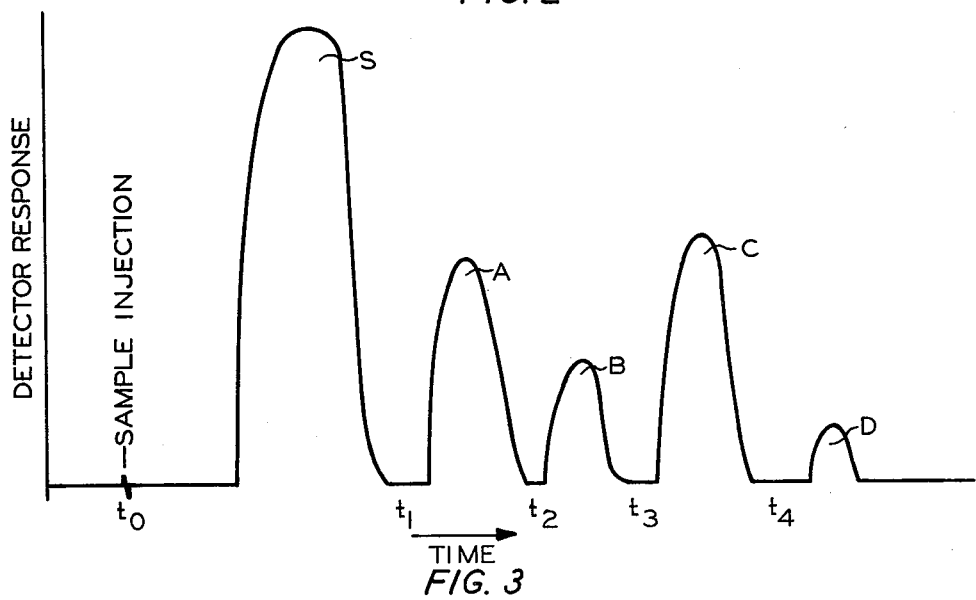
FIG. 3 is a schematic representation of the detector response of the apparatus of FIG. 1.

FIG. 3 illustrates the response of the detector 41, as embodied in the detector output signal 46, of the chromatographic analysis system of FIG. 1 where a bypass column 35 is used in parallel combination with the chromatographic separation column 33. Although the chromatographic peaks A, B, C, and D representative of constituents or groups of constituents within the sample fluid separated by elution through the chromatographic separation column 33 are received in the same relative order and at the same relative times, the presence of the bypass column 35 having the preferred flow characteristics previously described, results in an additional peak S appearing in the chromatographic output between the sample injection time $t_0$ and the time $t_1$ at which the first elution of sample constituents through the chromatographic separation column 33 is detected. Because the detector response forming the peak S results from an unresolved sample portion containing representative amounts of each of the various sample constituents and groups of constituents, consideration of each of the following peaks A, B, C, D, and any others which may be resolved, in light of the information on relative sample size available from the peak S, will permit a quantitative determination of the amount of each sample constituent or group of constituents represented by the peak as soon as the peak is received. For example, the determination of the material represented by peak A can be made at any time after time $t_2$. Similarly, by times $t_3$ and $t_4$ accurate quantitative determinations of the presence of constituents represented by peaks B and C respectively can be made.

Figure 4:
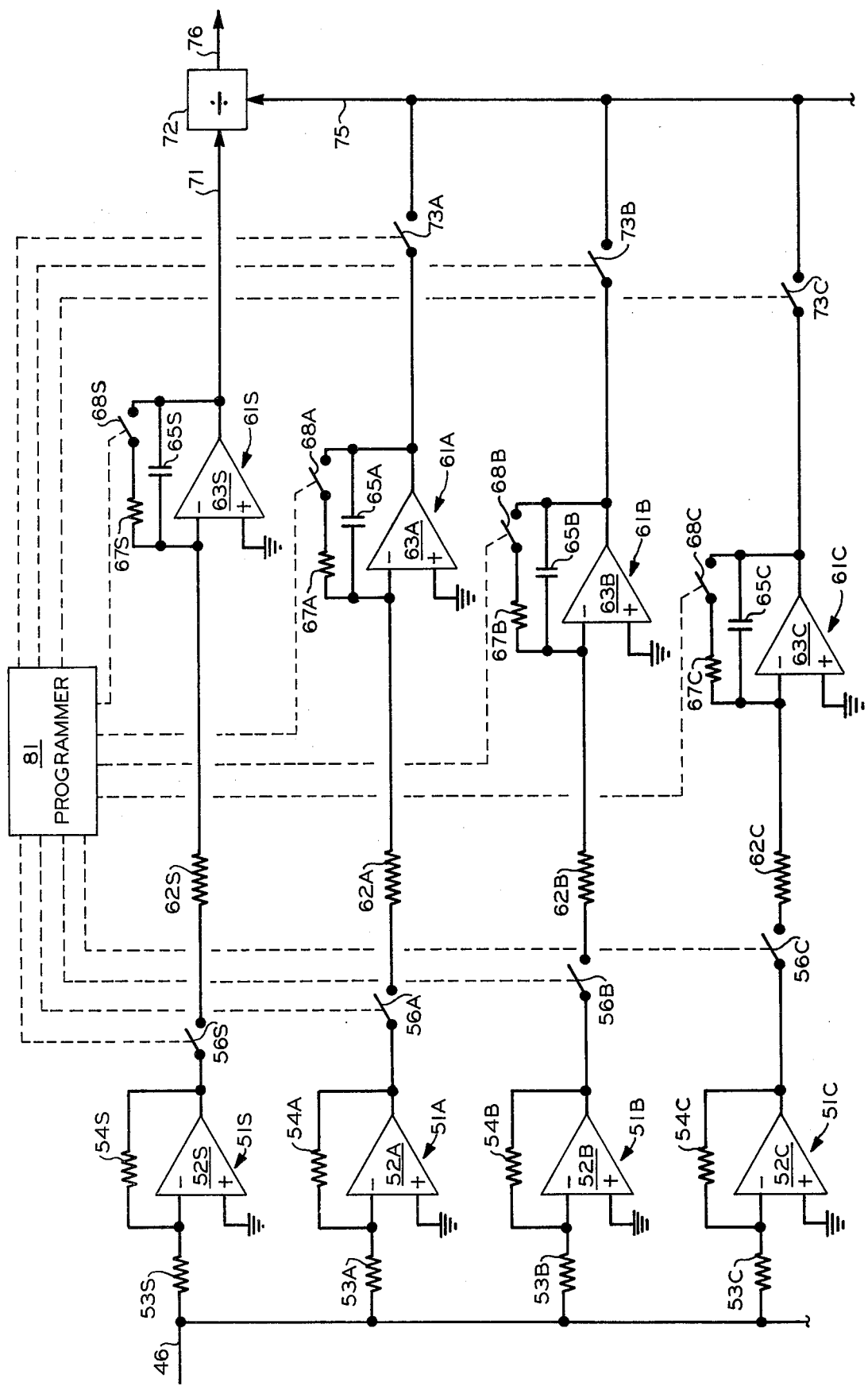
FIG. 4 is a schematic representation of an electronic circuit suitable for accepting the output signal from the detector of FIG. 1 and producing a plurality of normalized constituent signals responsive thereto.

While any suitable means for utilizing the information contained in the chromatographic detector response to sample constituents from the bypass column 35 and chromatographic separation column 33 can be utilized, automatic analysis means have the advantage of providing unattended operation and can be used to particular advantage when automatic control of a continuous process is based on automatic periodic analysis of process fluids. FIG. 4 illustrates a preferred circuit by which automatic normalization of the information provided by the chromatographic detector response can be accomplished. In accordance with the circuit of FIG. 4, the electrical output signal 46 from the detector means 41 is received and applied to a plurality of scaling amplifier circuits 51S, 51A, 51B, 51C . . . . Each of the scaling amplifiers comprises an operational amplifier 52S, 52A, 52B, 52C . . . having the noninverting input thereto connected to ground and receiving at the inverting input thereto, through a first scaling resistor 53S, 53A, 53B, 53C . . . , the detector output signal 46. A second scaling resistor 54S, 54A, 54B, 54C . . . is connected between the output of each respective operational amplifier and the inverting input thereof with the relative values of the two scaling resistors, specifically the resistance of the second or feedback resistor divided by the resistance of the first or input resistor, being determinative of the scaling factor applied by each scaling amplifier. The output of each scaling amplifier circuit is also connected to one terminal of a respective switch means 56S, 56A, 56B, 56C . . . , closure of which supplies the output of the associated scaling amplifier to a respective integrating circuit 61S, 61A, 61B, 61C . . . .

Each integrating circuit 61S, 61A, 61B, 61C . . . comprises a respective input resistor 62S, 62A, 62B, 62C . . . through which an input signal from the respective associated switch means 56S, 56A, 56B, 56C . . . is supplied to the inverting input terminal of an operational amplifier 63S, 63A, 63B, 63C . . . , the noninverting input of each amplifier being connected to ground. An integrating capacitor 65S, 65A, 65B, 65C . . . connects the output of each respective operational amplifier of the integrating circuit to the inverting input terminal thereof. Connected in parallel with each integrating capacitor is the series combination of a respective resetting resistor 67S, 67A, 67B, 67C . . . with a resetting switch means 68S, 68A, 68B, 68C . . . . When the resetting switch means is closed, the associated integrating capacitor is discharged through its resetting resistor to bring the signal at the output of the respective operational amplifier to zero.

The output of the integrating circuit 61S is provided as an input signal 71 to a divider circuit 72 for use as an input signal representative of the magnitude of the denominator of the dividing circuit 72. The outputs of each of the integrating circuits 61A, 61B, 61C . . . are applied to respective switch means 73A, 73B, 73C . . . so that closure of the associated switch means will provide the output signal from each of the respective integrating circuits as an input signal 75 to the divider 72, the divider 72 being adapted to accept the signal 75 for use in determining the magnitude of the numerator to be used in the division performed therein.

The divider means 72 can be any suitable means for accepting a numerator signal 75 and the denominator signal 71 and delivering in response thereto an output signal 76 representative of the division of the numerator signal 75 by the denominator signal 71.

A programmer means 81 is utilized to control the operation of switch means 56S, 56A, 56B, 56C . . . ; reset switches 68S, 68A, 68B, 68C . . . ; and switch means 73A, 73B, 73C . . . in a predetermined timed relationship, such timed relationship being coordinated with the passage of sample portions and separated sample constituents through the bypass column 35 and the chromatographic separation column 33 to the detector means 41. For example, at or shortly following time $t_0$ switch means 56S is closed while switch means 56A, 56B, 56C . . . remain in an open position. At this time switches 68S, 68A, 68B, 68C . . . will be closed or will have been closed in order to initialize the outputs of each integrating circuit 61S, 61A, 61B, 61C . . . at a zero value and will be opened prior to closure of respective switches 56S, 56A, 56B, 56C . . . in order to permit operation of the associated integrator circuit. Switch means 73A, 73B, 73C . . . are also in an open position at time $t_0$.

As the signal 46 detector response to the passage of sample fluid from the bypass conduit 35 is received by the scaling amplifier 51S, it is scaled by proper choice of resistors 53S and 54S during standard calibration runs, to provide as the output of the operational amplifier 52S a signal which is representative of the size of the sample introduced by the sample valve 11 into the analysis conduit 32 of the chromatographic apparatus. Application of this output signal from the scaling amplifier means 51S through the switch means 56S to the integrating circuit 61S will result in production of a signal 71 at time $t_1$ equal to the area under the curve S of FIG. 3. Since the area under a chromatographic peak or, in other terms, the integral of the detector response is known to bear a specific relationship to the amount of sample material detected, the value of signal 71 at time $t_1$ is representative of the amount of total sample material introduced into the chromatographic analysis system.

At time $t_1$ switch means 56S is opened and switch means 56A is closed. The opening of switch 56S halts any further input into the integrator 61S and the value of the output signal 71 of the integrator 61S is maintained at the value present at time $t_1$. Closure of switch means 56A at time $t_1$ starts integration by the integrator 61A of the detector output signal designated as peak A in FIG. 3, and integration in this manner continues until time $t_2$. At time $t_2$ the output of the integrator 61A is representative of the constituent or group of constituents represented by the peak A of FIG. 3 contained within the sample fluid analyzed. At time $t_2$, therefore, the switch means 56A is opened to terminate input to the integrator 61A of the scaled detector output signal 46 provided thereto, thereby maintaining the output of the integrator means 61A equal to the value of the area under the peak A of FIG. 3. At time $t_2$ switch means 56B is closed and, in a manner similar to that previously described with respect to the operation of integrator means 61A, the integrator means 61B begins integrating the portion of the scaled detector output signal representative of peak B of FIG. 3. At time $t_3$ when peak B has been received, switch 56B is opened and switch 56C is closed in order to maintain the scaled area under peak B as the output of integrator 61B and to begin the integration of the scaled area under peak C by integrator means 61C. This procedure can be continued and extended to as many peaks as may be of interest in any particular chromatographic analysis procedure with each successive scaling amplifier 51A, 51B, 51C in combination with its respective integrating means 61A, 61B, 61C . . . providing a scaled integral signal representative of the amount of preselected constituents or groups of constituents within the sample fluid.

At any time after time $t_2$, switch means 73A can be closed to provide a signal representative of the amount of the constituent or group of constituents represented by peak A as signal 75 to the dividing means 72. Since the signal 71 has already been provided by the integrating means 61S a signal 76 representative of the normalized value of the constituents represented by peak A is available as soon as the switch means 73a is closed any time after time $t_2$. In a similar manner, closure of switch 73B at any time after time $t_3$ of closure of switch means 73C at any time after time $t_4$ will result in the generation of a signal 76 representative of the normalized amounts of the constituents represented by peaks B or C. In order to prevent production of extraneous or confusing signals, only one of switches 73A, 73B, 73C . . . is closed at any given time. The means for initiating closure of switch means 73A, 73B, 73C . . . (not shown) can also be used to provide sampling of signal 76 when signal 76 is representative of the amount of those sample constituents of interest for experimental, analysis, or control purposes and to provide such signals to appropriate equipment.

Following the completion of delivery of the respective output signals of integrating means 61A, 61B, 61C by the associated switch means 73A, 73B, 73C to the divider 72, and following the completion by the dividing means 72 of all activity associated with a particular analysis cycle, resetting switches 68S, 68A, 68B, 68C . . . can be closed to reset the outputs of respective integrators 61S, 61A, 61B, 61C . . . to zero in preparation for the next analysis cycle. Resetting of the various integrators can therefore be accomplished as soon as the information from that integrator is no longer needed for subsequent use by the divider 72 or at the end of the analysis cycle when all previous values can be reset in preparation for a succeeding analysis.

While the circuit illustrated by FIG. 4 utilizes a separate scaling amplifier 51S, 51A, 51B, 51C for each chromatographic peak, it is, of course, within the scope of the invention to use a single scaling amplifier as the source of signal to a plurality of switch means 56S, 56A, 56B, 56C . . . . One such alternate example would be the use of a scaling amplifier 51S along with a single additional scaling amplifier performing the function of amplifiers 51A, 51B, 51C . . . . Additionally, under circumstances where the flow rates through the bypass conduit 35 and the chromatographic separation conduit 33 are equal, a single scaling amplifier could be used to perform the desired scaling function for all signals to be integrated or, all scaling amplifiers 51S, 51A, 51B, 51C ... could be omitted from the circuit.

In addition to its functions in controlling the switching associated with the separate integration of various portions of the detector signal 46, the programmer 81 can be utilized to initiate chromatographic analysis cycles by controlling operation of the sample valve 11 and by performing such other timed or analysis-dependent switching or programming operations as may be desirable.

Components suitable for use in accordance with the illustrated preferred embodiment of the invention of FIGS. 1 and 4 are as follows:

| | |
|---|---|
| Sample valve 11 | Model IX valve manufactured by Applied Automation, Inc. Bartlesville, OK 74004 |
| Pumps 22 and 27 | Pump number 82-S-35 manufactured by Sprague Engineering P. O. Box 430 Gardena, Calif. 90248 |
| Chromatographic separation column 33 | Stainless steel tube 25 cm. in length, ¼ inch O.D. packed with a material which would cause some delay to all constituents of the particular sample, such as Lichrosorb S160, 5 micron size, manufactured by E. M. Laboratories, Inc. 500 Executive Blvd. Elmsford, N.Y. 10523 |
| Bypass column 35 | 25 cm. in length, ¼ inch O.D. with packing which would cause no chromatographic separation, such as glass beads |
| Detector means 41 | Refractive Index Detector part number A55002 manufactured by Applied Automation, Inc. Bartlesville, OK 74004 |
| Amplifiers 52S, 52A, 52B, 52C...; 63S, 63A, 63B, 63C... | Burr-Brown low bias current amplifier No. 3542, manufactured by Burr-Brown Research Corp., Tucson, Arizona 85734 |
| Divider 72 | Analog Devices Divider AD530 manufactured by Analog Devices, Inc., Norwood, Mass. 02062 |
| Programmer 81 and associated switches | Programmer Model 102, manufactured by Applied Automation, Inc. Bartlesville, OK 74004 |
| Resistors 53S, 53A, 53B, 53C... | 10 K ohm |
| Resistors 54S, 54A, 54B, 54C... | Selected to give proper scaling |
| Resistors 62S, 62A, 62B, 62C... | 10 K ohm |
| Resistors 67S, 67A, 67B, 67C... | 100 ohm |
| Capacitors 65S, 65A, 65B, 65C... | 10 microfarad |

One example of an application of the method and apparatus of the invention using alternate separation and bypass columns with the remainder of the apparatus being the same as listed above would be the determination of the relative constituent amounts in a stream containing isobutane, n-butane, 1-butene, isobutylene, trans-2-butene, cis-2-butene, and 1-3-butadiene. For this analysis, a suitable separation column is ⅛ inch O.D. stainless steel tubing four feet in length packed with 10% by weight bis[2-(2-methoxyethoxy)ethyl]ether (Eastman Kodak Company, Rochester, N.Y.) on a 80% by weight substrate of Chromosorb P (Johns-Mansville Company) based on the total weight of packing material. Using this particular separation column, the seven components of the sample will elute in six peaks with 1-butene and isobutylene eluting together in a single peak. A bypass column suitable for use with such a separation column is 1/16 inch O.D. stainless steel open, unpacked tubing two feet in length. At specific times following injection of the sample, a large unseparated peak from the bypass column will be seen by the detector followed by six successive peaks from the separation column. With the first unseparated peak being provided to the denominator of the divider, the normalized proportion of each constituent, or group of constituents in the case of 1-butene and isobutylene, can be determined as each of the following six peaks is received and provided to the numerator of the dividing circuit. There is no need to backflush the separation column to determine the amount of other possible slow-eluting constituents in the sample prior to generating a signal representing the normalized proportion of a specific constituent in the sample, or is there any need to wait for all constituents to elute prior to generating a signal representing the normalized relative proportion of an early eluting constituent in the sample. In addition, analysis for one or more key constituents can be terminated as soon as the key constituents arrive at the detector with the most expeditious procedure available under the circumstances being used to clear the separation column in preparation for a subsequent analysis.

While the invention has been described in conjunction with the presently preferred embodiments thereof reasonable variations and modifications are possible by those skilled in the art within the scope of the invention and of the appended claims thereto.

We claim:

1. A method for determining the proportionate amounts of chromatographically separable constituents within a material, said method comprising:

introducing a sample of said material into a carrier fluid in a chromatographic separation apparatus;

passing carrier fluid containing a first portion of said sample through a bypass conduit means to a sample detection means;

passing carrier fluid containing a second portion of said sample through a chromatographic separation column to said sample detection means; said bypass conduit means containing packing material capable of presenting a resistance to flow but incapable of seriously delaying any of the sample constituents, said bypass conduit means being of such length and of such restriction to flow that the flow rate of carrier fluid and sample fluid therethrough bears a predetermined relationship to the flow rate of carrier fluid and sample fluid through said chromatographic separation column and that said first portion of said sample passes through said sample detection means prior to arrival of any portion of said second portion of said sample at said sample detection means;

generating, in response to the output of said sample detection means, a first signal from which information can be obtained indicative of the total amount of sample material in said first portion of said sample;

generating, in response to the output of said sample detection means, at least one second signal, each said second signal being a signal from which information can be obtained indicative of the amount of a respective selected constituent or group of constituents separated from the remaining constituents of said second portion of said sample by said chromatographic separation column; and generating, in response to said first signal and each respective one of said at least one second signals, a corresponding number of third signals, each said third signal being associated with a respective one of said second signals and being a signal from which information can be obtained indicative of the relative amount of the respective said constituent or group of constituents represented by the respective second signal present within said sample of said material.

2. A method in accordance with claim 1 comprising generating, in response to said first signal and a plurality of said second signals, a plurality of said third signals, each said third signal being associated with a respective one of said second signals.

3. A method in accordance with claim 2 wherein generating said first signal comprises generating a signal proportional to the total amount of sample material, and wherein generating each said second signal comprises generating a signal proportional to the amount of the respective said constituent or group of constituents in said sample material.

4. A method in accordance with claim 3 wherein generating each said third signal comprises dividing the respective second signal by said first signal.

5. A method in accordance with claim 1 wherein generating said first signal comprises integrating the output of said sample detection means during the time that said first portion of said sample is passing therethrough, and wherein generating each said second signal comprises integrating the output of said sample detection means during the time that the respective said selected constituent or group of constituents is passing therethrough.

6. A method in accordance with claim 5 wherein generating said first signal comprises generating a signal proportional to the total amount of sample material, and wherein generating each said second signal comprises generating a signal proportional to the amount of the respective said constituent or group of constituents in said sample material.

7. A method in accordance with claim 6 wherein generating each said third signal comprises dividing the respective said second signal by said first signal.

8. A method in accordance with claim 1 wherein the ratio of the flow rate of said first portion to the flow rate of said second portion is in the range of 1:10 to 1:1.

9. A method in accordance with claim 1 wherein the ratio of the flow rate of said first portion to the flow rate of said second portion is about 1:1.

10. Apparatus comprising:
a chromatographic separation column means;
a bypass column means connected in parallel with said chromatographic separation column means and containing packing material capable of presenting a resistance to flow but incapable of seriously delaying any of the sample constituents, said bypass column means being sized to provide a bypass flow bearing a predetermined relationship to the flow through said separation column means and to provide for passage of fluid through said bypass column means in a shorter time than required for passage of fluid through said separation column means;
means for injecting a fluid sample material into a fluid carrier stream flowing to the parallel combination of said separation column means and said bypass column means;
detector means for receiving the combined fluid output of said parallel combination and detecting the presence of said fluid sample material therein;
first means responsive to said detector means for producing a first signal representative of the amount of sample material flowing through said bypass column means;
at least one second means responsive to said detector means for producing a second signal, each said second signal being representative of the amount of a respective preselected constituent or group of constituents eluted through said separation column means; and
third means responsive to said first means and each respective one of said at least one second means for producing a corresponding number of third signals, each said third signal being associated with a respective one of said second signals and being representative of the relative amount of the respective preselected constituent or group of constituents within said fluid sample.

11. Apparatus in accordance with claim 10 wherein said bypass column means and said separation column means are sized to provide substantially the same resistance to fluid flow under operating conditions.

12. Apparatus in accordance with claim 10 wherein said third means comprises means for dividing each of a plurality of said second signals by said first signal.

* * * * *